United States Patent [19]
Boehringer et al.

[11] Patent Number: 4,781,707
[45] Date of Patent: Nov. 1, 1988

[54] PROCESS AND APPARATUS FOR COLLECTING BLOOD FROM A BODY CAVITY FOR AUTOTRANSFUSION

[75] Inventors: John R. Boehringer, Wynnewood; John Karpowicz, Glenmoore, both of Pa.

[73] Assignee: Boehringer Laboratories, Wynnewood, Pa.

[21] Appl. No.: 906,750

[22] Filed: Sep. 12, 1986

Related U.S. Application Data

[63] Continuation-in-part of Ser. No. 830,577, Feb. 18, 1986.

[51] Int. Cl.⁴ .............................................. A61M 1/00
[52] U.S. Cl. .................................... 604/317; 604/319
[58] Field of Search ......... 137/205; 604/321, 317–320

[56] References Cited

U.S. PATENT DOCUMENTS

| | | | |
|---|---|---|---|
| 3,363,626 | 1/1968 | Bidwell et al. | 128/276 |
| 3,363,627 | 1/1968 | Bidwell et al. | 128/276 |
| 3,559,647 | 2/1971 | Bidwell et al. | 128/276 |
| 3,680,560 | 8/1972 | Pannier et al. | 128/276 |
| 3,683,913 | 8/1972 | Kurtz et al. | 128/276 |
| 3,704,709 | 12/1972 | Sorenson et al. | 128/277 |
| 3,809,085 | 5/1974 | Bidwell et al. | 128/275 |
| 3,853,128 | 12/1974 | Kurtz et al. | 128/275 |
| 3,863,634 | 2/1975 | Reynolds et al. | 128/276 |
| 3,866,608 | 2/1975 | Reynolds et al. | 128/276 |
| 4,018,224 | 4/1977 | Kurtz et al. | 604/321 |
| 4,105,031 | 8/1978 | Kurtz et al. | 604/321 |
| 4,372,336 | 2/1983 | Cornell et al. | 604/321 |
| 4,439,190 | 3/1984 | Protzmann et al. | 604/319 |
| 4,443,220 | 4/1984 | Hauer et al. | 604/408 |
| 4,455,141 | 6/1984 | Todd | 604/321 |
| 4,465,483 | 8/1984 | Weilbacher | 604/317 |
| 4,519,796 | 5/1985 | Russo | 604/319 |

FOREIGN PATENT DOCUMENTS 8400489  10/1984  PCT Int'l Appl. ................. 604/321

OTHER PUBLICATIONS

Chapter 4/Drainage Apparatus; pp. 67–97, The Pleural Space.
Sorensen Research advertisement for Drainage Device in Medical Electronic Products Magazine.
W. L. Gore and Associates, Inc. brochure for Gore-Tex Membrane Products.
Emerson brochure for Disposable Thoracic Drainage Sets.
Arglye brochure for Chest Drainage Unit.
Chesebrough—Pond's Inc. brochure for Thora-Drain III Chest Drainage System.

(List continued on next page.)

Primary Examiner—John D. Yasko
Assistant Examiner—J. L. Kruter
Attorney, Agent, or Firm—Paul & Paul

[57] ABSTRACT

A process for the collection of blood from a body cavity requires a controllable flow conduit having an inlet and an outlet. The inlet of the conduit is placed in a body cavity from which blood is to be withdrawn. The outlet of the conduit is connected to the inlet of a blood collection apparatus. The apparatus includes an apparatus body having a first opening therein for connection to a source of suction and a gas-transmitting water seal. The apparatus also includes an autotransfusion collector for collecting and storing blood for optional blood reuse. The collector includes an outer receptacle and an inner receptacle. The inner receptacle includes at least one interior cavity and at least one substantially flexible wall at least partially enclosing the at least one interior cavity. The apparatus also includes a conduit for placing the source of suction in fluid communication with the interior cavity through the water seal. An inlet conduit communicates with the interior cavity and the body cavity for carrying blood to the inner receptacle when suction is applied to the first opening in the apparatus body. Preferably, the outer receptacle is substantially rigid and the collector further includes at least one intermediate cavity between the outer receptacle and the inner receptacle. In a preferred embodiment the intermediate cavity is sealed against fluid communication with the atmosphere.

46 Claims, 12 Drawing Sheets

OTHER PUBLICATIONS

Halkey Medical advertisement for Luer Style Syringe Check Valve.
Davol Inc. instructions for Chest Drainage Unit.
Howmedica, Inc., instructions for Pleur-Evac Chest Drainage Unit.
Ohio Medical Products brochure for Thoracic Drainage System.
Becton–Dickinson brochure for Suction Collection Canister.
Deknatel brochure for Pleur-Evac ® Autotransfusion System Insert.
Deknatel brochure for Pleur-Evac ® A-4000 Adult-Pediatric System.
Thoratec Medical Incorporated operating instructions for Bloodstat TM Autotransfusion System.

PROCESS AND APPARATUS FOR COLLECTING BLOOD FROM A BODY CAVITY FOR AUTOTRANSFUSION

CROSS-REFERENCE TO RELATED APPLICATION

This is a continuation-in-part of U.S. patent application Ser. No. 830,577, filed Feb. 18, 1986, by John R. Boehringer, John Karpowicz and Steven T. Sutter, and assigned to a common assignee.

BACKGROUND OF THE INVENTION

1. Field of the Invention

This invention relates to a process and apparatus for collecting shed blood from body cavities during surgical procedures and the like, and more particularly this invention relates a process and an apparatus for collecting shed blood for autotransfusion.

2. Brief Description of the Prior Art

Self-contained, disposable systems for the collection, anti-coagulation, filtration and reinfusion of blood shed into body cavities are known. Autotransfusion permits a patient's own shed blood to be recycled during the course of an operation. Autotransfusion is especially useful when appropriate banked blood is unavailable or when the patient's religious convictions, technical complications, or other factors dictate than banked blood not be used.

Prior art autotransfusion processes and apparatus often require that blood collected at a surgical site be stored in a first blood reservoir nad subsequently transferred to a second blood reservoir or blood bag, and also often require complicated priming and blood transfer procedures. These complicated procedures require expensive apparatus and increase the risk of error causing harm to the patient.

Other types of drainage units or devices for collecting fluids from body cavities are also known in the art. Initially, such devices comprised a plurality of bottles connected by hoses. One such bottle would form the collection chamber for matter being drawn from a body cavity and another bottle would form a water seal through which gases from the collection chamber would be bubbled and to which a source of suction would be connected. A third bottle could be employed as a manometer for monitoring and controlling the amount of vacuum, or negative pressure of the system, to a given pressure corresponding to a predetermined height of a column of water. These systems have gradually developed into disposable, single unit systems in which a plurality of internally connected chambers functioned as collection chambers, water seals and manometers.

In addition, it is known to employ such unitary drainage devices as sources of suction of collection of blood into specially adapted blood bags which are externally supported against collapse during blood collection. An example of an externally supported blood bag for collecting shed blood by suction is provided in U.S. Pat. No. 4,443,220 which discloses a collapsible sterilizable collection bag in combination with a special stent adapted to hold the bag in distended form as blood is collected in the presence of a vacuum in the bag. However, this system suffers from a major deficiency in that the vacuum in the interior of the bag must be released after blood collection in order to dislodge the bag from the stent. This release of vacuum could conceivably introduce ambient air into the interior of the bag. The ambient air may contain dangerous microorganisms which may contaminate the collected blood and render it unfit for transfusion back into the patient's body.

There is a clear need for an autotransfusion process and device which takes advantage of the simplicity and economy of unitary drainage devices as sources of suction for blood collection vessels which are releasably supported against pressure differential-induced collapse during blood collection, but which employ support means which are readily disengageable without requiring prior venting of the interior of the blood collection vessel to the atmosphere.

In other types of disposable devices for collecting body fluids, such as disclosed in U.S. Pat. Nos, 3,680,560, 3,685,517, and 3,866,608, a rigid cannister envelops an inner receiver formed from a rigid cap for the cannister sealed to a flexible liner for the cannister. Provision is made to actively exert a suction on the volume between the liner and the cannister to prevent the liner from collapsing when suction is applied within the liner to draw fluid into the liner. Providing means to create the countervailing suction increases the complexity and cost of manufacture of the device. Further, unless a separate port and suction line are provided for the countervailing suction, releasing suction to disassemble the device requires admitting air into the liner, thus increasing the risk of contamination of blood collected therein. On the other hand, using a separate port and suction line to provide a countervailing suction increases the complexity and cost of the apparatus, and further increases the complexity of operation of the device. There is a need for an apparatus and process which simplify the blood collection process, decreasing the complexity of the procedures required to collect blood for optional blood reuse and reducing the likelihood of operator error associated with prior art collection devices and procedures.

SUMMARY OF THE INVENTION

The present invention is directed toward providing a novel process and apparatus directed toward overcoming the above deficiencies in prior art autotransfusion processes and devices, as well as offering additional improvements.

It is a primary object of this invention to provide a simple, inexpensive apparatus and a simple associated process for the collection of blood for transfusion back into the body from which the blood was obtained.

It is a further object of this invention to provide a process for autotransfusion of blood employing a disposable, easy-to-use apparatus having reduced likelihood of blood contamination in comparison with prior art processes and apparatus.

Yet another object of this invention is to provide a disposable apparatus for blood collection requiring simpler, more economical fabrication techniques than prior art devices.

It is also an object of the present invention to provide a simplified process for collecting blood for optional later blood reuse, the process requiring fewer steps than prior art processes and consequently reducing the likelihood of operator error.

Another object of this invention is to provide an economical apparatus for the collection of blood for optional later blood reuse which provides means for collecting overflow from the primary collection vessel so that blood collection need not be interrupted to substitute collection vessels when a first vessel has been filled to capacity. This provides the operator with additional flexibility and provides the option of deferring the substitution of a new collection vessel should the operator be required to attend to other matters during blood collection.

Another object of this invention is to provide an improved apparatus for blood collection wherein, in case of accidental upset of the device, flow back from other portions of the apparatus into the primary blood collection vessel is avoided.

A still further object of the present invention is to provide an improved apparatus for blood collection for optional later blood reuse having a blood collection vessel which is releasably supported against pressure differential-induced collapse during blood collection, but which employs support means which are readily disengageable without requiring prior venting of the interior of the blood collection vessel to the atmosphere.

It is another object of the present invention to provide a blood collection apparatus having a sealing means for trapping air-borne contamination when the device is disconnected from a source of suction.

Another object of the present invention is to provide a blood collection apparatus having pressure control means which permits an operator to control the magnitude of suction provide to the apparatus from an external source of suction.

A further object of the present invention is to provide a blood collection apparatus which permits sampling of collected blood from the collection vessel for diagnostic testing and the like.

Another object of the present invention is to provide a blood collection apparatus having a plurality of blood collection vessels which may be filled sequentially without interrupting the flow of blood to the apparatus.

A still further object of the present invention is to provide an improved autotransfusion blood collection apparatus having a disposable blood collection vessel which may be used with standard infusion sets to deliver blood to a patient.

Another object of the present invention is to provide an improved blood collection apparatus which may be quickly and easily fitted with a detachable blood collection vessel which, when filled, can be quickly replaced with an empty vessel.

The process of the present invention requires a controllable flow conduit having an inlet and an outlet. The inlet of the controllable flow conduit is placed in a body cavity from which blood is to be withdrawn. The outlet of the controllable flow conduit is connected to the inlet of a blood collection apparatus to place the body cavity in fluid communication with the blood collection apparatus.

The blood collection apparatus includes an apparatus body having a first opening therein for connection to a source of suction and a blood collection means for collection and storing blood from the body cavity. The apparatus further includes a gas-transmitting sealing means having a first and second side, the first side being in fluid communication with the first opening. Air is drawn through the sealing means from the second side to the first side, thereby creating a partial vacuum proximate the second side of the sealing means. Suitable apparatus bodies including sealing means are disclosed in U.S. patent application Ser. No. 830,577, now pending, filed Feb. 18, 1986, which is incorporated herein by reference.

The apparatus of the present invention in a first presently preferred embodiment includes blood collection means including at least one autotransfusion collector for collecting and storing blood for optional blood reuse. The autotransfusion collector includes an outer receptacle and an inner receptacle, the inner receptacle being positioned substantially within the outer receptacle. The inner receptacle includes at least one interior cavity and at least one substantially flexible wall at least partially enclosing the interior cavity. The apparatus further includes means for placing the second side of the sealing means in fluid communication with the interior cavity of the autotransfusion collector for drawing a vacuum thereon. The autotransfusion collector further includes an inlet conduit means in fluid communication with the interior cavity of the inner receptacle. The inlet conduit is adapted for communication with the body cavity for carrying blood therefrom to the inner receptacle when suction is applied to the first opening in the apparatus body.

The process employing this apparatus further includes the steps of applying suction to the first opening in the apparatus body and subsequently opening the first control means in the controllable flow conduit to permit blood to flow from the body cavity, through the controllable flow conduit, and into the inner cavity of the inner receptacle.

Blood which has been collected in the autotransfusion collector can be subsequently used for transfusion back into the patient from which it was obtained.

In the first presently preferred embodiment, the outer receptacle of the autotransfusion collector is substantially rigid and the autotransfusion collector further includes at least one intermediate cavity between the outer receptacle and the inner receptacle. The intermediate cavity is sealed against fluid communication with the atmosphere, thus maintaining the inner receptacle in a substantially uncollapsed condition during collection of blood therein.

Other objects and advantages of the present invention will be readily understood from a reading of the foregoing as well as the description of the drawings, as well as other explanation of the invention as will appear hereinafter.

BRIEF DESCRIPTION OF THE DRAWINGS

FIG. 4 is a fragmentary cross-sectional view of the apparatus of FIG. 4 taken generally along the line V—V of FIG. 4.

FIG. 5 is a fragmentary front elevational view of a third embodiment of the apparatus of the present invention.

FIG. 8 is a fragmentary cross-sectional view of the apparatus of FIGS. 6 and 7 taken generally along the line VIII—VIII of FIGS. 6 and 7.

DETAILED DESCRIPTION OF THE PREFERRED EMBODIMENTS

Figure 1:
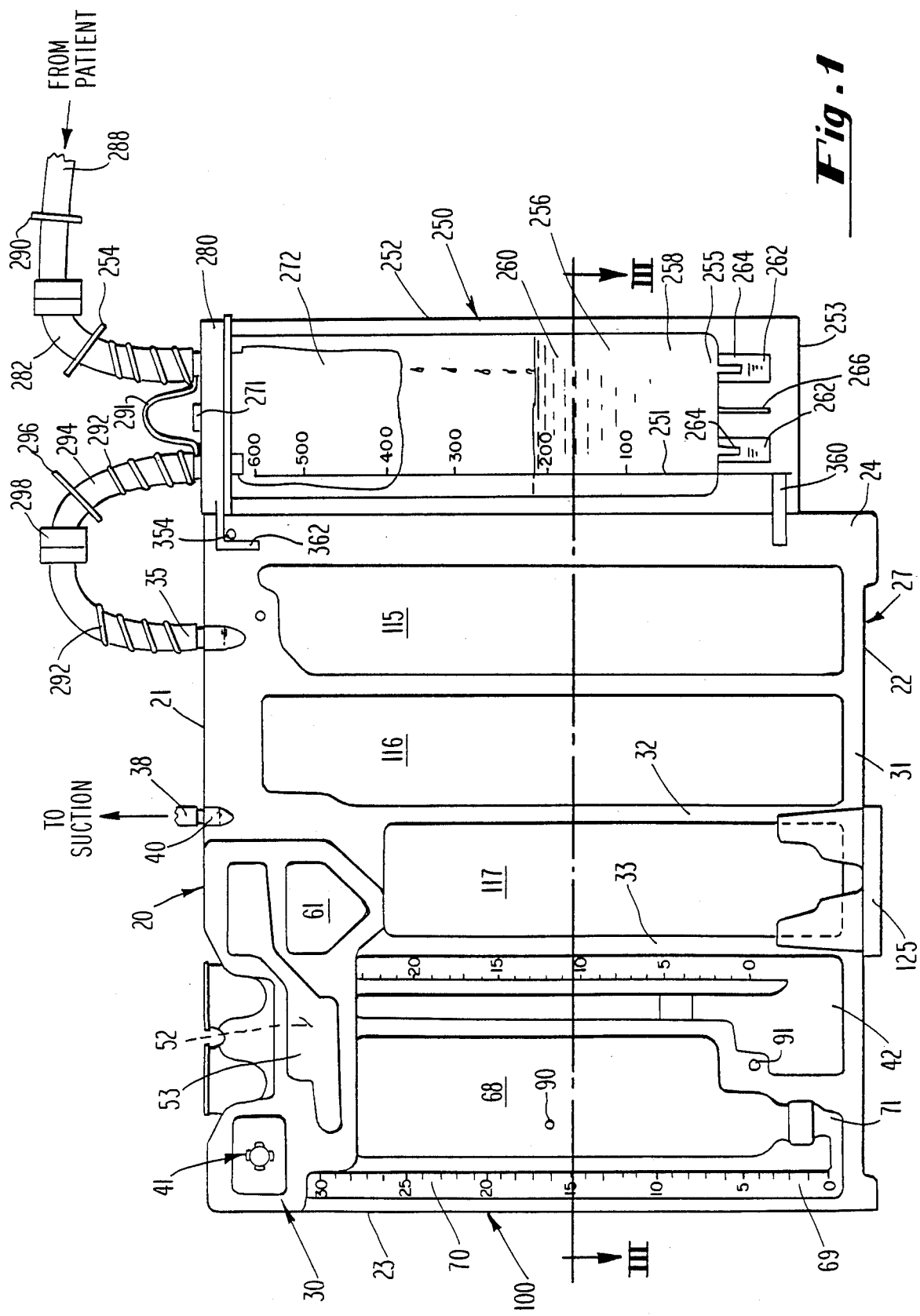
FIG. 1 is a front elevation view of a first embodiment of the blood collection apparatus of the present invention.

Referring now to the drawings in detail, reference is first made to FIG. 1, wherein the first presently preferred embodiment of an apparatus according to the present invention, generally designated by the numeral 20, is shown in vertical or upstanding disposition. The apparatus includes an apparatus body 100 to which is detachably connected an autotransfusion collector 250.

The apparatus body 100 can be a drainage device for collecting liquids from a body cavity such as that disclosed in the commonly assigned U.S. patent application Ser. No. 830,577 now pending filed Feb. 18, 1986 and discussed in detail therein. In the present embodiment the apparatus body 100 has upper and lower ends 21, 22 and left and right ends 23, 24 as illustrated in FIG. 1. The apparatus body can be constructed of various materials and formed in various ways, such as by vacuum forming, injection molding or blow molding of a thermally formable plastic material or the like. In the present embodiment the principal components of the apparatus body 100 include front and back molded members 27, 28 (FIG. 3) and an additional molded member 30 at the upper left corner of FIG. 1. These members are secured together along various flanges such as, but not limited to those 31, 32, 33 by means of suitable heat sealing, adhesive, and/or solvent sealing techniques generally known in the art. Preferably, at least one of the front and back molded members 27, 28 is formed from a transparent or translucent material permitting the interior of the apparatus body 100 to be viewed by an observer. The apparatus body 100 includes a removable base 125 which securely supports the upstanding apparatus 100 against accidental falling forward or backward or tipping over.

The apparatus body 100 includes a plurality of chambers formed between the molded members 27, 28, 30. The chambers include a water seal chamber 42, first, second and third overflow chambers 115, 116, 117 and a manometer chamber 69. The function, construction and use of the various chambers in the apparatus body 100 are described in detail in U.S. patent application Ser. No. 830,577. However, the structure and function of each of these chambers are also described briefly below.

The apparatus body 100 includes a first opening 40 formed therein for connection to a source of suction (not illustrated) through a vacuum line 38. The vacuum line 38 will generally be connected to a customary hospital supply, provided through a regulated wall outlet or the like, and adjusted to 90–100 mm. Hg. of vacuum, or any other suitable vacuum. In addition, a second opening 41 to the atmosphere is formed in the apparatus body 100 for drawing ambient air from the atmosphere into the apparatus body 100 as needed as described below.

A gas-transmitting sealing means includes water contained within a water seal chamber 42. The water seal chamber 42 is provided at the lower end of the apparatus body 100 between generally vertically disposed conduits 43, 44 which respectively include first and second sides of the sealing means. The water level in the water seal chamber 42 will generally be at the level shown by the dotted line 45 (FIG. 2), which corresponds to the level of the "O" designation shown in FIG. 1, to allow about 2 cm. of distance "D" for air or other gases to pass through the water seal means. Air or gas drawn through the water seal means travels in the direction indicated by the arrow 46, along conduit 44, around the lower end 48 of separation wall 47 between the conduits 43 and 44, and up conduit 43 and into conduit zone 50, into interconnecting conduit 52 (FIG. 1) formed by the wall 53 of the additional molded member 30 sealingly disposed against front wall member 27, into air/gas withdrawal zone 55 and out through first opening 40.

Figure 2:
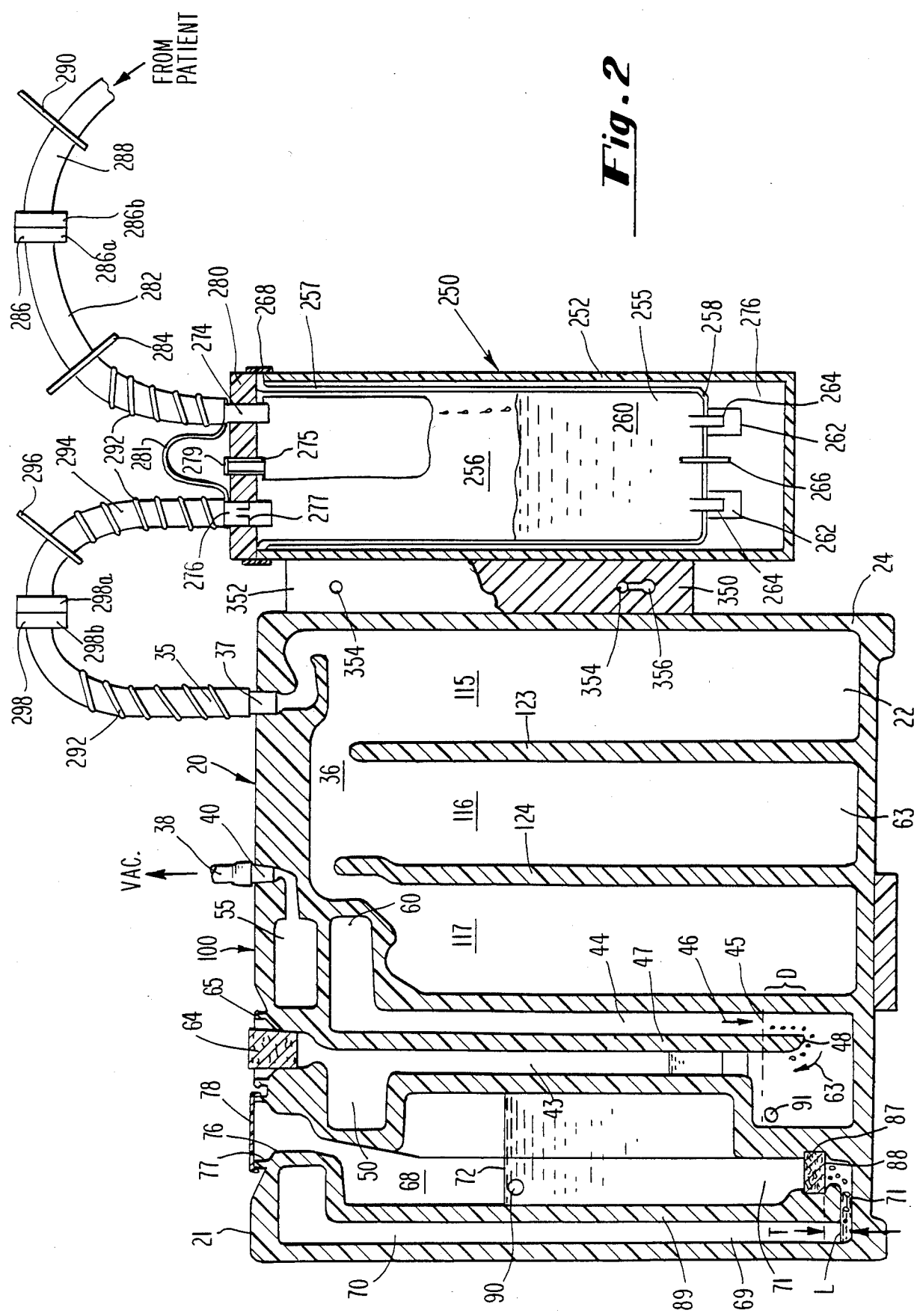
FIG. 2 is a vertical sectional view a blood collection apparatus of the present invention illustrating an alternative means of mounting the autotransfusion collector to the apparatus body.

As best seen in FIG. 2, air/gas is drawn into the apparatus body 100 through a third aperture or inlet opening 37 fitted with a conduit 35 formed from flexible tubing. The inlet opening 37 and the conduit 35 are adapted for placing the second side of the sealing means in fluid communication with the autotransfusion collector 250 as described below. The inlet opening 37 opens into a first overflow chamber 115. The first, second and third overflow chambers 115, 116, 117 together comprise a collection chamber 36 for blood which overflows into the apparatus body 100. The collection chamber 36 is in fluid communication through a chamber 61 (FIG. 1) formed in the additional molded member 30 with the second water seal vertical conduit 44 (FIG. 2) through a zone 60. Thus, the apparatus body 100 includes means for placing the second side of the sealing means in fluid communication with the inlet opening 37 through a series of internal chambers formed in the apparatus body 100.

As best seen in FIG. 2, the apparatus body 100 includes a U shaped manometer chamber 69 having two legs or chambers 68, 70 and filled with a manometer liquid 72 such as water. A first leg or chamber 70 of the manometer chamber 69 is in fluid communication with the atmosphere through the second opening 41 in the apparatus body 100. The second leg or chamber 68 is in fluid communication through chamber 52 (FIG. 1) formed in the additional molded member 30 with the air/gas withdrawal zone 55 (FIG. 2) and through first opening 40 with the source of suction. By drawing vacuum through conduit 38, the low pressure created in the air/gas withdrawal zone 55 relative to atmospheric pressure outside the second opening 41 maintains a desired predetermined water level 72 in the manometer chamber 71, which can be visually determined relative to a predetermined desired water pressure, by reference to the numbered chart at the left end of the apparatus body 100 illustrated in FIG. 1. Generally, a level 72 at least half way up the chamber 69 is desired. The level of water in the manometer chamber 69 thus determines the amount of control for the suction provided by the vacuum source, to a predetermined height of water pressure, such as 20 cm. of water pressure, or the like.

With reference to FIG. 2, it will be noted that the manometer chamber 69 is provided with a bubble breaker 86 shown seated in a molded seat 87 at the lower end thereof, disposed at a predetermined distance "T" above the bottom of chamber 69 such that air bubbles entering the liquid in the manometer chamber 69 below the level "L" have a short distance to travel (approximately 1 cm.) upwardly after passing along the lower end of manometer separation 89, such distance "T" being sufficient to enable the bubbles to attain enough velocity to break when they strike against the bubble breaker 86.

The first leg 68 is initially filled through a water inlet opening 77 sealed by a cap 78. Fine adjustments in the water level may be made through access opening or port 90 using an appropriate tool, such as a needleless syringe. Similarly, the water seal chamber 42 can be filled through an opening 65 formed above the first water seal vertical conduit 43 which can thereafter be sealed with a stopper 64 or cap (not illustrated). In addition, fine adjustments in the level of fluid in the water seal chamber 42 can be affected through a second sealing port 91.

Figure 11:
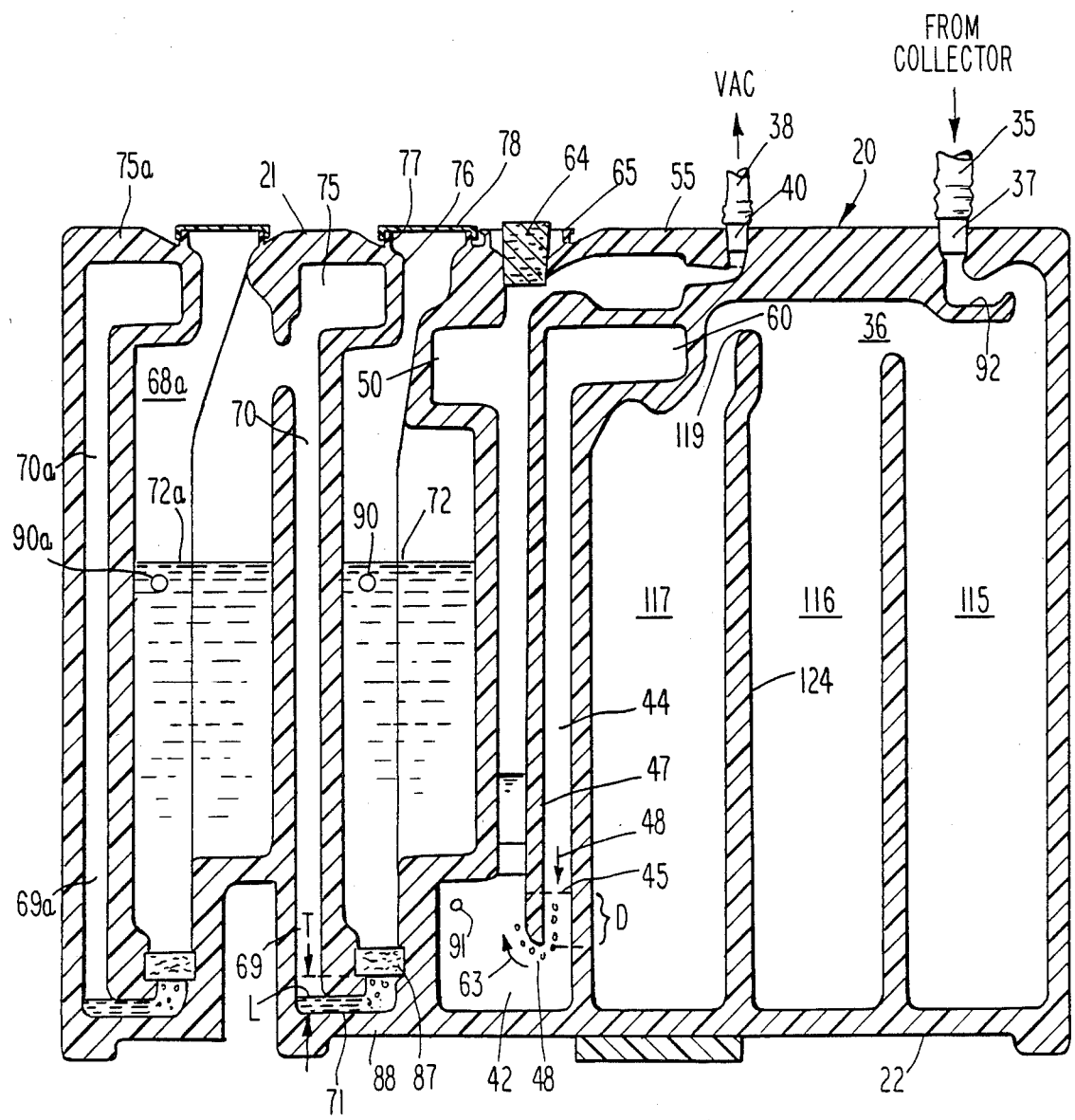
FIG. 11 is a fragmentary front elevational view of an apparatus body of the present invention having plural manometer chambers.

As shown in FIG. 11, the apparatus body 100 can include a plurality of manometer chambers 69, 69a connected in series so that elevated levels of suction may be easily and reliably controlled with an apparatus body 100 having a predetermined height. In this case, the second leg 70 of the first manometer chamber 69 is in communication with the first leg 68a of the second manometer chamber 69a, and not with the atmosphere. However, the second leg 70a of the second manometer chamber 69a is in communication with the atmosphere (not shown).

Figure 3:
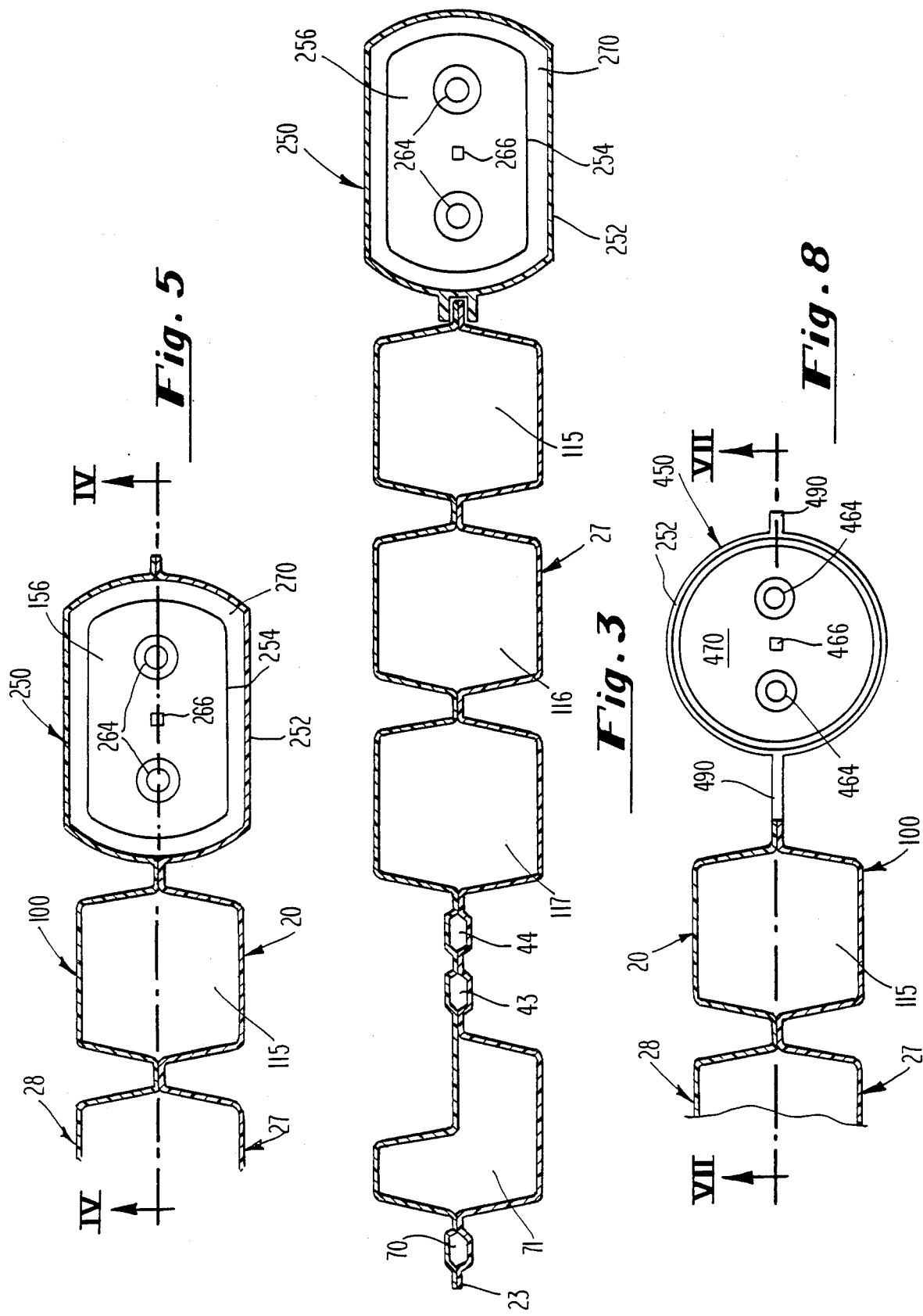
FIG. 3 is a cross-sectional view of the apparatus of FIG. 1, taken generally along the line III—III of FIG. 1.
Figure 12:
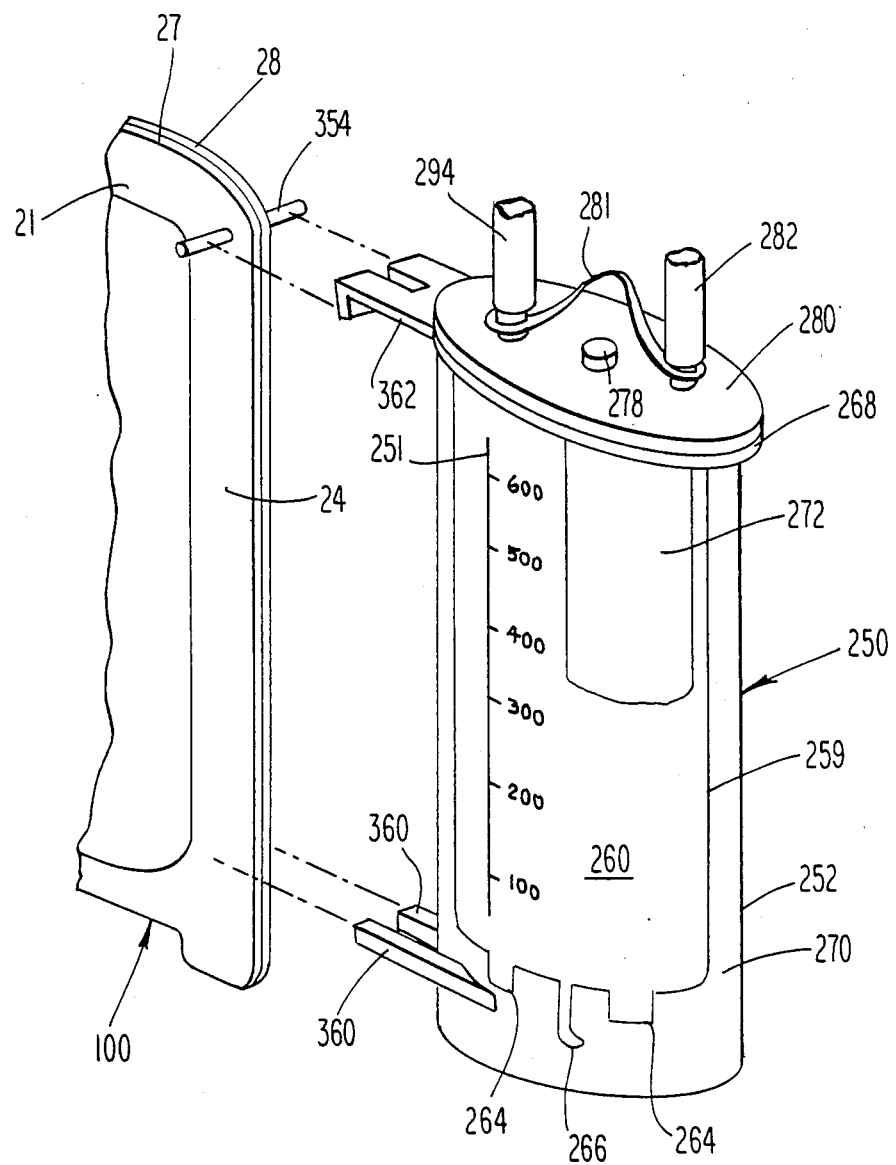
FIG. 12 is an expanded, exploded fragmentary perspective view of the apparatus of FIG. 1.

As shown in FIG. 1 in the first preferred embodiment of the apparatus of the present invention, the apparatus 20 includes an autotransfusion collector 250 detachably connected to the apparatus body 100. The autotransfusion collector 250 comprises blood collection means for collecting and storing blood from a body cavity for optional blood reuse. FIGS. 1, 3, and 12 show one manner of releasably securing the autotransfusion collector 250 to the apparatus body, while FIG. 2 illustrates a slightly different attachment means.

The autotransfusion collector 250 includes a generally tubular outer receptacle 252 having a closed end 253 and formed from a substantially rigid and generally transparent or translucent material. Preferably, the outer receptacle 252 is formed from a rigid, breakage-resistant thermoplastic material. The inner receptacle preferably includes a scale 251 molded therein, printed thereon, or otherwise affixed thereto to gauge the liquid contained within the autotransfusion collector 250 as it is filled. A convenient writing strip can be provided near the scale on the outer receptacle 252 for noting start time, quantity per unit time, and other information relating to blood collection (not shown).

The outer receptacle 242 further includes a pair of parallel, spaced, generally horizontally projecting lower fingers 360 (FIGS. 1 and 12) to aid in attaching the autotransfusion collector 250 to the apparatus body 100 as described below. Alternatively, as shown in FIG. 2 in a slightly modified version of the embodiment of FIGS. 1, 3, and 12, the outer receptacle 252 can include a generally annular vertically extending flange 350 having a plurality of slots 356 formed therein for mounting the autotransfusion collector 250 on a corresponding support flange 352 formed on the right side 24 of the apparatus body 100. The support flange 352 has a plurality of pins 354 projecting perpendicularly from the support flange 352 and positioned to correspond to the slots 356, as illustrated in FIG. 2.

The autotransfusion collector 250 further includes an inner receptacle or blood bag 254. The inner receptacle 254 is positioned substantially within the outer receptacle 252 and includes an interior cavity 256 for collecting and storing blood 260. An intermediate cavity 270 is formed between the inner receptacle 254 and the outer receptacle 252. The inner receptacle 254 includes a substantially flexible wall 258 closing the interior cavity 256. The wall 258 can be formed from a standard blood bag of the type used to bank blood, such as a multi-port blood bag formed from polyvinyl chloride or the like. As best seen in FIG. 3, in this embodiment the cross-section of the wall 258 is generally elliptical. The wall 258 has a sealed end 255 and an expanded end 257.

The inner receptacle 254 includes a plurality of sealed ports or spike ports 264 and associated tabs 262 for transfusion of collected blood 260 back into a body cavity of the patient from which the blood 260 has been obtained as described below. In addition, the sealed end 25 includes a hanger 266 such as is conventionally provided on flexible blood bags.

In addition, the inner receptacle 254 includes a substantially rigid cap 280 to which the wall 258 is sealed at the bottom of the cap 280 proximate the periphery of the cap 280. The cap 280 is releasably sealed in a hermetic air-tight manner to the outer receptacle 252 by receptacle sealing means or seal 268 (best seen in FIG. 2) which surrounds a portion of the periphery of the cap 280 and a portion of the exterior of the upper end of the outer receptacle 252. The seal 268 may be formed of any suitable material such as a heat-shrinkable thermoplastic material, and can include an adhesive bonding material to affix the seal 268 to the cap 280 and the outer receptacle 252.

Preferably, the autotransfusion collector 250 is formed to minimize the volume of the intermediate cavity or cavities 270 formed between the flexible wall 258 of the inner receptacle and the outer receptacle 252. To this end, the closed end 253 of the outer receptacle 252 can be formed to closely conform to the exterior topology of the sealed end 255 of the wall 258 of the inner receptacle 254 (not illustrated). Alternatively, portions of the interior cavity 256 may be filled with an inert space-filling material preferably having a transparent or translucent character to further reduce the effective volume of the intermediate cavity 270. For example, portions of the interior cavity 270 can be filled with glass microballoons, transparent plastic pellets, or the like (not illustrated). In any case, it is preferable to minimize the ratio of the gas volume of the intermediate cavity 270 to the interior cavity 256 of the inner receptacle 254. Alternatively, or in addition, the intermediate cavity 270 can be at least partially evacuated during manufacture of the autotransfusion collector 250. In this case, both the outer receptacle 252 and the inner receptacle 254 are preferably formed from materials having low gas permeability so that the partial vacuum in the intermediate cavity 270 is maintained during storage of the apparatus 20 prior to use.

Figure 4:
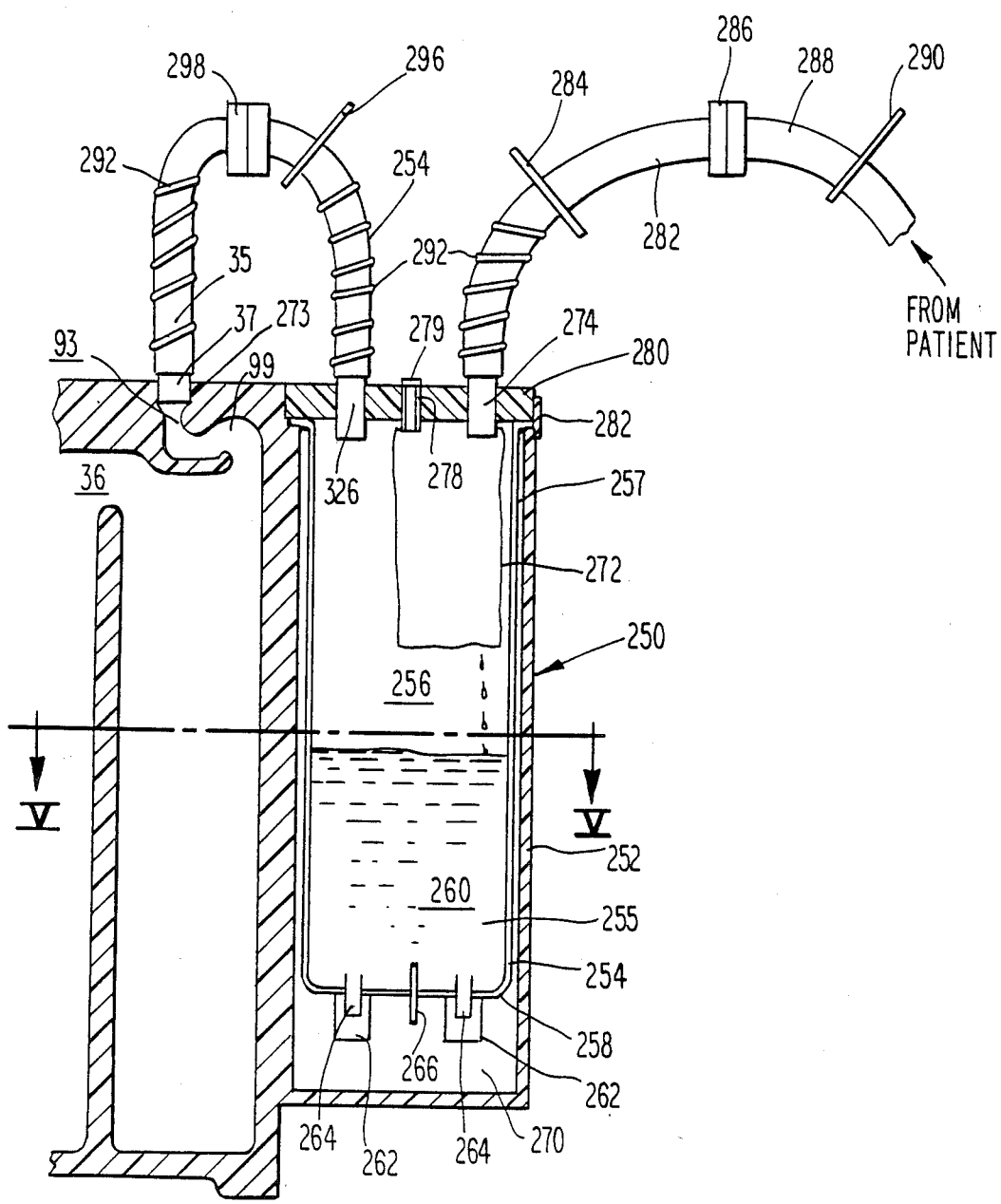
FIG. 4 is a fragmentary vertical sectional view of a second embodiment of the apparatus of the present invention taken generally along the line IV—IV of FIG. 5.
Figure 13:
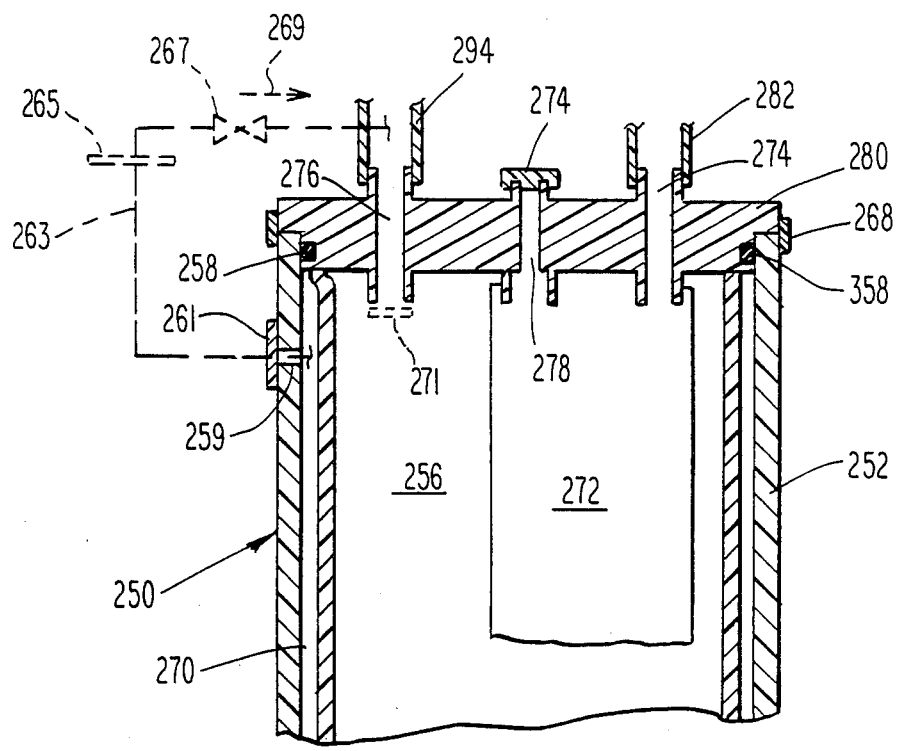
FIG. 13 is an expanded, fragmentary vertical sectional view of an apparatus of the present invention showing a sealing gasket between an inner receptacle and an outer receptacle.

In addition to the seal 268, which can be a pressure-sensitive tear strip adapted to be easily removed by an operator, the receptacle sealing means can include a gasket 358 such as an "O"-ring formed from a fluoroelastomer positioned in confronting grooves between the cap 280 of the inner receptacle 254 and the outer receptacle 252 as shown in FIG. 13, a ring seal formed in the outer periphery of the cap 280 (not illustrated), or the like. Optionally, a vent port 259 can be provided to vent the zone or intermediate cavity 270 to atmosphere, upon removal of seal 261. An an additional option, a vacuum communication line 263 is shown in phantom in FIG. 13 for drawing a vacuum between the collection receptacle 254 and the intermediate cavity or zone 270, in the manner of U.S. Pat. No. 3,704,709 to Sorenson, the complete disclosure of which is herein incorporated by reference, in instances where it is not desired to maintain a hermetic seal between zone 270 and the interior of inner receptacle 254. Alternatively, when the autotransfusion collector 250 is integral with an adjacent chamber, such as shown in FIG. 4, the vent port 259 may facilitate the continuous vacuum draw from the upper end of the adjacent chamber, preferably through a hydrophobic seal. As a further option, FIG. 13 schematically illustrates in phantom the use of a one-way-flow check valve 267, with flow in the direction of arrow 269 only, in the line 263, in series with a hydrophobic filter 265 (similar to hydrophobic filter from our patent application Ser. No. 830,577), the filter allowing an air flow but not liquid flow from the zone 270 to outlet 276. Additionally, if desired, a hydrophobic filter 271 may prevent blood or other liquids from cavity 256 from flowing into outlet 276 upon upset. Similarly, with reference to FIG. 4, a hydrophobic filter 273 may allow air to be drawn through it, but may prevent liquid flow from other chambers to interior cavity 256 upon upset.

The autotransfusion collector 250 further includes an inlet conduit or blood inlet 274 formed in the cap 280 and adapted for communication with a body cavity for carrying blood therefrom to the inner receptacle 254 when suction is applied to the first opening 40 in the apparatus body 100. A controllable flow conduit extends between the body cavity and the inlet of the blood collection apparatus 20. The controllable flow conduit includes at least one section of flexible wall tubing 288, and is provided with a first control means or first clamping means 290. The controllable flow conduit is terminated at one end with a first portion 286a of a first connecting means 286. A mating, detachable second portion 286b of the first connecting means 286 terminates the inlet to the blood collection apparatus 20, which also includes a second section of flexible tubing 282, and second control means or second clamping means 284.

The first control means 290 is adapted to control the flow of blood through the first flexible tubing section or delivery tube 288 from the body cavity to the first connecting means 286. The second control means 284 is adapted to control the flow of blood through the second flexible tubing section or inlet tube 282 linking the first connector means 286 and the inlet conduit means 274 to the inner receptacle 254. If desired, the control means 284, 290 can be adjusted to clamp the corresponding sections of flexible tubing 282, 288 shut to prevent fluid flow therethrough.

The end of the inlet conduit means 274 inside the inner receptacle 254 is fitted with a filter 272 of conventional construction to strain foreign matter and the like from the blood 260 flowing into and being collected within the autotransfusion collector 250.

The apparatus 20 of the present invention further includes means for placing the second side of the sealing means in fluid communication with the interior cavity 256 of the autotransfusion collection 250. As best seen in FIG. 2, an outlet conduit means 276 is formed in the cap 280 to which is attached an outlet tube 294 in the form of a section of flexible tubing. A check valve 277 is preferably fitted within the outlet conduit means 276 to prevent backflow of blood from the apparatus body 100 to the autotransfusion collector 250. However, the check valve 277 permits suction to be applied to the interior cavity 256 and also permits overflow of blood 260 from the interior cavity 256 of the inner receptacle 254 to the overflow chamber 36 in the apparatus body 100.

A detachable second connector means 298 is fitted to the other end of the outlet tube 294 and a third control means or third clamping means 296 is positioned on the outlet tube 294 intermediate the second connector means 298 and the outlet conduit means 276 for controlling flow through the outlet tube 294. Yet another section of flexible tubing comprises the inlet conduit 35 to the apparatus body 100 and extends between the second connector means 298 and the inlet opening 37 through the apparatus body 100. Each of the sections of flexible tubing 282, 294, 35 extending from the cap 280 of the autotransfusion collector 250 or the apparatus body 100 is preferably fitted with an antikinking means or exterior spring 292 which is adapted to prevent accidental clamping or sealing of the flexible tubing by bending thereof.

The cap 280 is also preferably fitted with a sampling port 278 having a self-resealing cap 279 adapted for permitting samples of the blood 260 to be withdrawn from within the interior cavity 256 without interrupting the blood collection process or for the addition of reagents or treatment liquid such a anti-coagulant solution to the blood 260 through the filter 272 contained within the inner receptacle 254.

A loop 281 extends between the inlet conduit means 274 and the outlet conduit means 276 and is securely affixed thereto. The loop 281 is adapted to suspend the autotransfusion collector 250 from a conventional IV stand or other suspension means when the blood 260 is being transfused into a body cavity.

As shown in FIG. 3, the cross-sectional shape of the outer receptacle 252 is preferably adapted to conform to the shape assumed by the wall of the inner receptacle 254. For example, when a conventional blood bag of the type used to store blood in blood banks is used in constructing the inner receptacle 254, the wall 258 has the cross-sectional shape of a flattened tube or generally elliptical shape. Preferably, the long axis of the generally elliptical shape is oriented parallel to the longitudinal axis of the apparatus body 100 to minimize the floor space required by the apparatus 20.

In this first embodiment of the apparatus of the present invention the autotransfusion collector 250 may be replaced when filled with blood 260 with a new autotransfusion collector 250. The autotransfusion collector 250 may be quickly and easily changed by clamping the first, second and third control means 290, 284, 296; disconnecting the first and second connector means 286, 298; and then detaching the autotransfusion collector 250 from the support means of the apparatus body 100.

In the version of the first embodiment of the apparatus illustrated in FIGS. 1 and 12 the cap 280 includes a pair of parallel spaced, generally "L"-shaped upper hooking fingers 362 extending parallel to the pair of lower fingers 360 extending from the outer receptacle 252 proximate the closed end 253 thereof. The upper hooking fingers 362 are adapted to releasably secure the autotransfusion collector 260 to the apparatus body 100 by hooking around either end of a pin 354 projecting perpendicularly through the right side 24 of the apparatus body 100 proximate the upper end 21 thereof.

Figure 14:
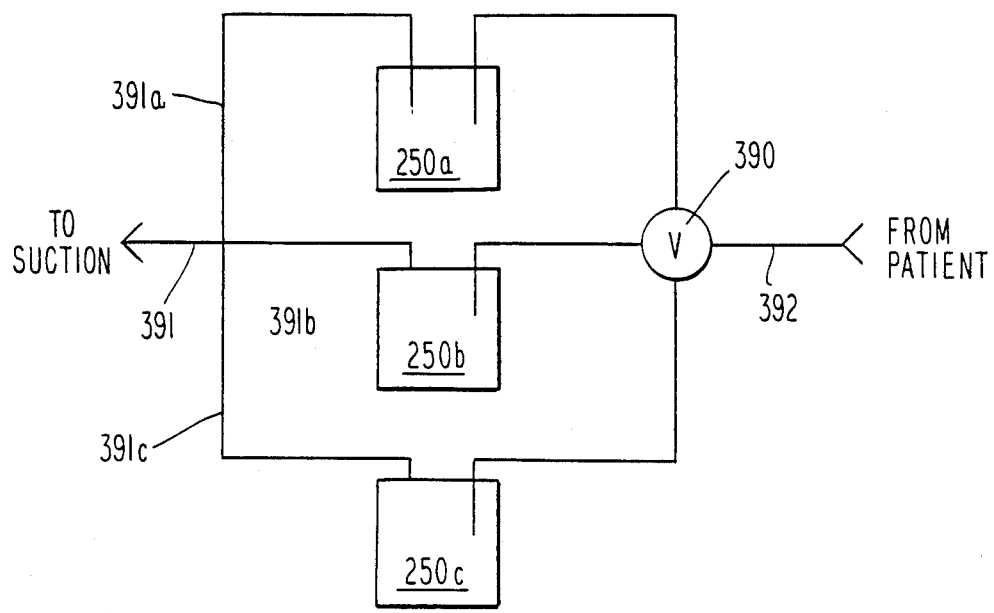
FIG. 14 is a partial schematic illustration of an apparatus of the present invention having plural autotransfusion collectors.

As schematically illustrated in FIG. 14, a plurality of autotransfusion collectors 250a, 250b, 250c may be used. Preferably, the inlet conduit means of the collectors 250a, 250b, 250c are connected to a valve means 390 for selectively placing the interior cavities of each of the collectors 250a, 250b, 250c in fluid communication with a flow conduit means 392 adapted to carry blood from a body cavity. Thus, each of the collectors 250a, 250b, 250c can be successively filled when suction is drawn at 391, and via a respective line 391a, 391b, or 391c, without disrupting the flow of blood from the body cavity.

FIGS. 4 and 5 illustrate a second embodiment of an apparatus 20 according to the present invention. In this second embodiment, the outer receptacle 252 of the autotransfusion collector 250 and the apparatus body 100 are formed as an integral whole. The front and back molded members 27, 28 of the apparatus body 100 each form a portion of the outer receptacle 252 as another chamber in the apparatus body 100. In this second embodiment of the apparatus 20, the apparatus 20 may be discarded, if desired, after the inner receptacle 254 has been withdrawn from the apparatus 20; alternatively, the apparatus 20 can be retained and replacement receptacles 254 may be used. However, in such latter instance, continuous vacuum draw of the type of FIG. 13 (phantom), or suitable mechanical supports for the receptacle, as are discussed herein, will be required.

Figure 6:
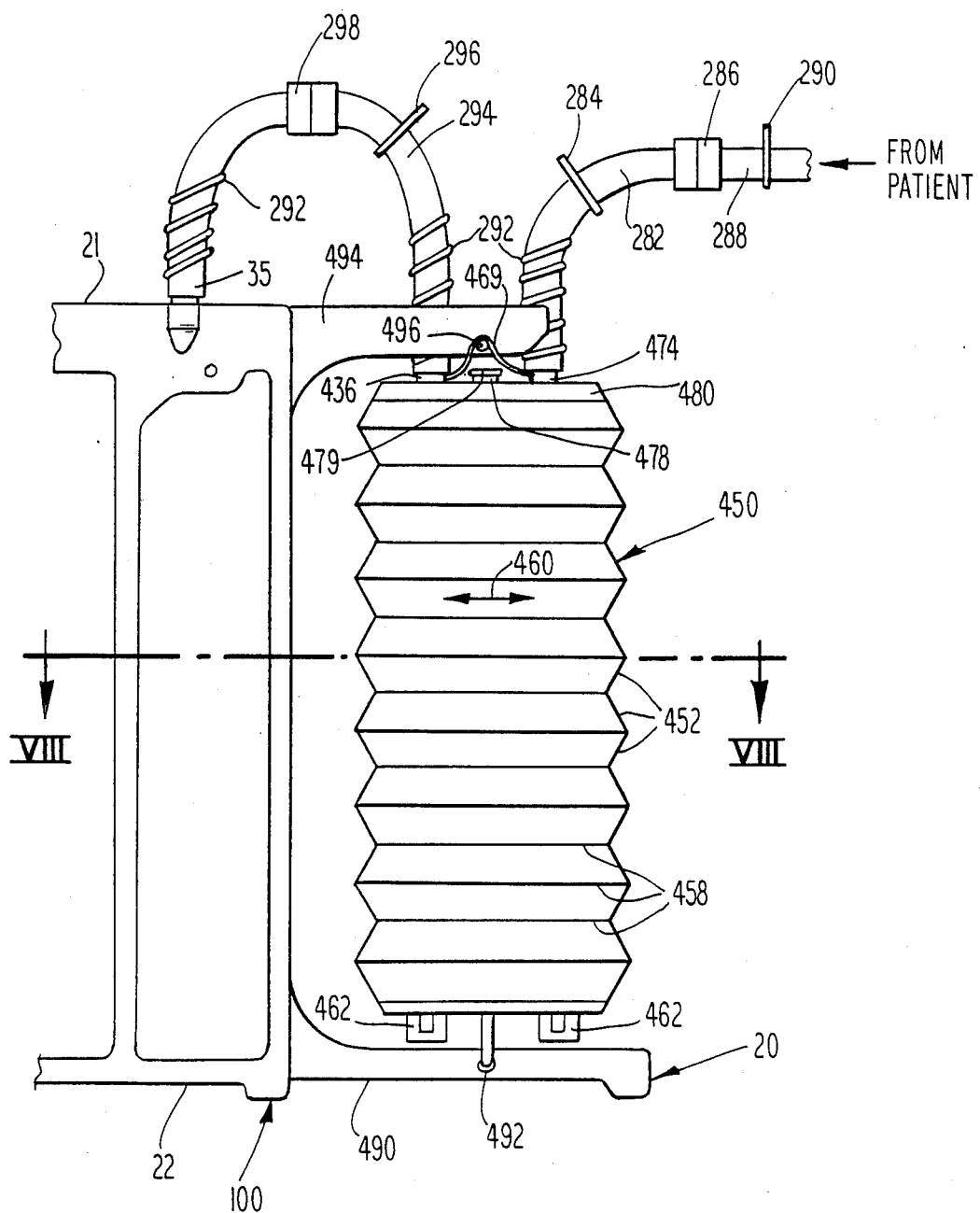
Figure 7:
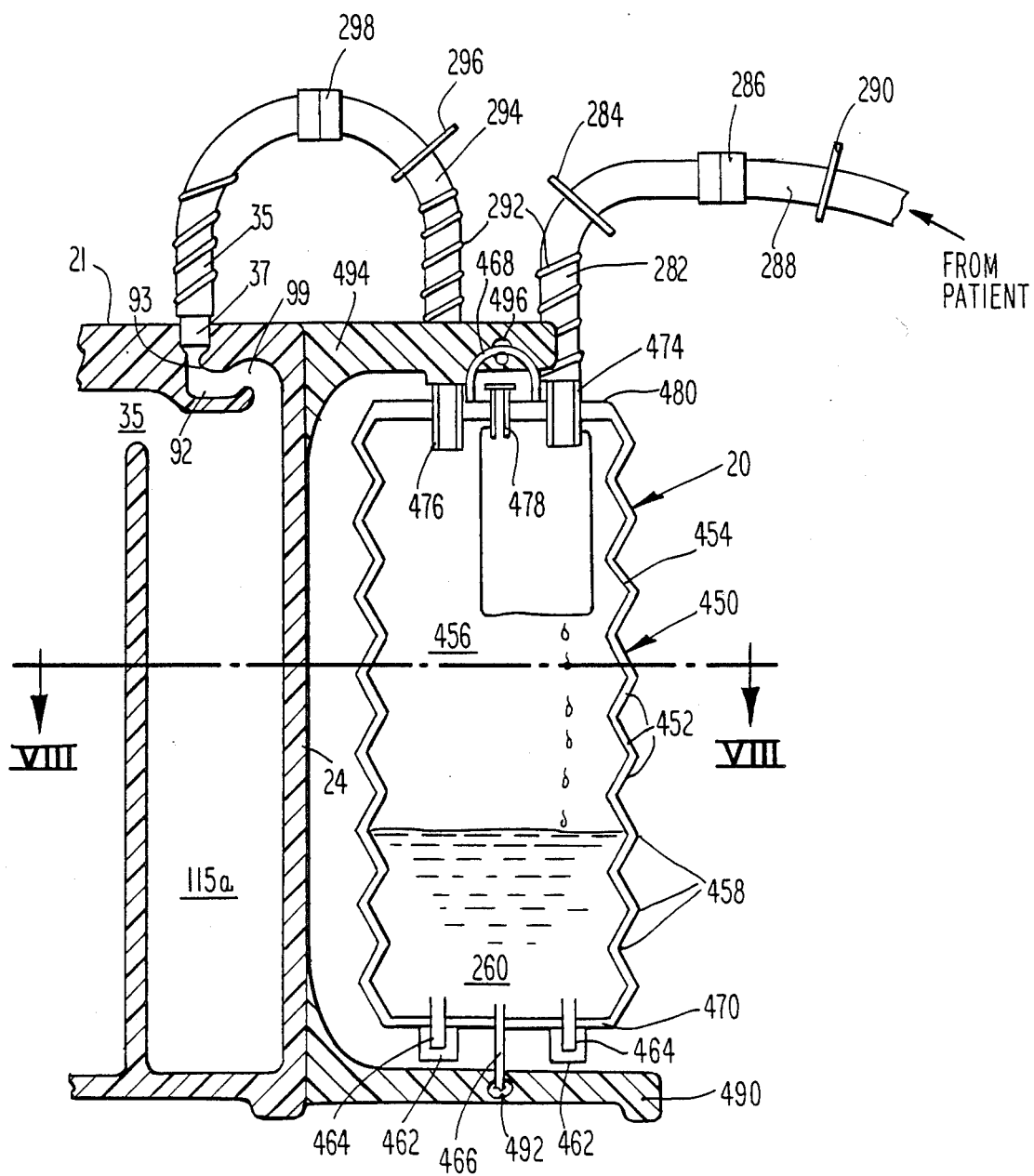
FIG. 7 is a fragmentary vertical sectional view of the apparatus of FIG. 6 taken generally along the line VII—VII of FIG. 8.

FIGS. 6–8 illustrate a third embodiment of the apparatus of the present invention. This embodiment employs an accordion collector 450 for collecting and storing blood 260 for optional later blood reuse in autotransfusion. The accordion collector 450 is suspended between a lower support member 480 and an upper support member 494 projecting from the right side 24 of the apparatus body 100 proximate the lower and upper ends thereof 22, 21 respectively.

The accordion collector 450 is a generally tubular receptacle for the blood 260 and has a wall 454 having a plurality of pleats 452. The direction of the pleats 452 is indicated by a double-headed arrow 460 in FIG. 6. The wall 454 is preferably formed form a relatively rigid material so that wall is relatively inflexible except at the creases 458 between the pleats 452. The pleats 452 permit the extension of the accordion collector 450 to be variable generally perpendicular to the direction of the pleats 452. The accordion collector 450 thereby encloses an interior cavity 456 of variable volume.

As shown in FIGS. 6 and 7, the pleats 452 extend generally horizontally when the accordion collector 450 is mounted in the apparatus 20. However, vertical pleats or pleats oriented in other directions may also be employed.

The accordion collector 450 includes a base 470 formed integrally with the pleated wall 454 and having formed therein a pair of sealed ports or spike ports 464 for delivery of blood 260 from the accordion collector 450 and associated tabs 462. In addition, the base 470 includes a lower support means or hanger 466 for releasably engaging an aperture 492 formed in the lower support member 490. The accordion collector 450 also includes an inlet conduit means or blood inlet 474 positioned in a cap 480, the cap 480 being preferably integrally formed with the wall 454 of the accordion collector 450. A blood filter 472 is fitted to the inlet conduit means 474 to filter blood collected and stored within the interior cavity 456 of the accordion collector 450. The cap 480 is also fitted with an outlet conduit means 476 for placing the interior cavity 456 in communication with the second side of the water seal and thence with a source of suction as in the apparatus of the first embodiment of the present invention (not illustrated). A sampling port 476 fitted with a self-sealing cap 479 is also positioned in the cap 480 of the accordion collector 450 for withdrawing samples of blood 260 contained therein or for adding reagents such as anticoagulants. As in the case of the first embodiment, an upper support means or loop 468 is provided on the cap 480. However, the loop 468 is employed to secure the upper end of the accordion collector 450 to a hook 496 projecting from the upper support member 494.

In use, the pleats 452 provide a transverse rigidity or strength to the accordion collector 250 when suction is applied to the interior cavity 456, while the attachments to the upper and lower support members 494, 490 resist collapse of the accordion collector 450 along the longitudinal axis thereof when suction is applied to the interior cavity 456. Thus, a significant pressure differential between the atmosphere and the interior cavity 456 can be tolerated by the accordion collector 450 without the requirement of a countervailing suction applied exteriorally of the wall 454 of the accordion collector 450 being required to maintain the volume of the interior cavity 456 relatively constant. Yet the upper and lower support means 468, 466 are easily releasable to permit the partially evacuated accordion collector 450 to collapse under atmospheric pressure when the desired amount of blood 260 has been collected. The support means 468, 466 may be released by the operator, for example, by simply disengaging the hanger 466 from the aperture 492 when desired.

Figure 9:
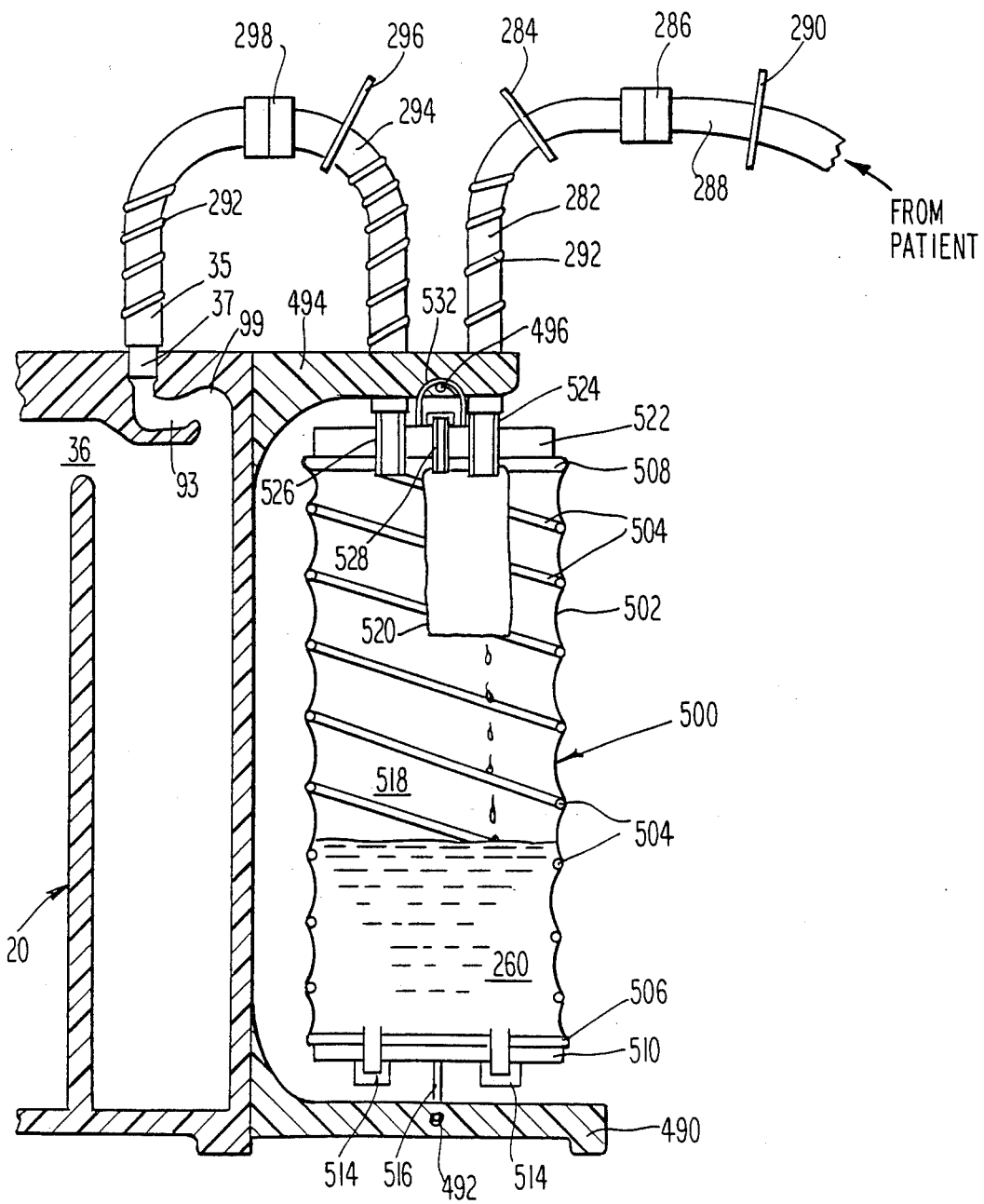
FIG. 9 is a fragmentary vertical sectional view of a fourth embodiment of the apparatus of the present invention.

A fourth embodiment of the apparatus of the present invention is illustrated in FIG. 9. In this embodiment means are provided for maintaining the receptacle for the blood in an extended configuration when a vacuum is drawn on the interior cavity of the receptacle, the support means being releasable to permit the partially-evacuated receptacle to collapse under atmospheric pressure, as in the case of the third embodiment of the apparatus. In this fourth embodiment a generally tubular receptacle having an interior cavity for the blood is employed; and the receptacle has two spaced, generally parallel substantially rigid ends and a wall extending between the ends. The wall is formed from a substantially flexible material. Preferably, first support means are adapted to support the wall against collapse in a direction generally parallel the ends when a vacuum is applied to the interior cavity of the receptacle. However, the first support means allow collapse of the receptacle in a direction perpendicular the ends.

As shown in FIG. 9, the first support means can include generally helical support members 504 extending from proximate one end of the receptacle to proximate the other end of the receptacle adjacent the wall 502 thereof. In the illustrated embodiment a pair of helical support members 504 extend from a lower ring 506 to an upper ring 508, respectively positioned proximate a substantially rigid base 510 and substantially rigid cap 522, giving a collector 500 having a generally helical shape. The helical support members 504 are disposed interiorally of a wall 502 formed from a substantially flexible material such as a transparent or translucent thermoplastic material. The wall 502 is sealed to the base 510 and cap 522 proximate the upper and lower ends of the wall 502. The base 510 includes sealed ports 512 and associated tabs 514 for use in delivery of blood 260 from the helical collector 500.

The base 510 includes a hanger 516 to releasably secure the lower end of the helical collector 500 to lower support member 490 by releasable engagement with aperture 392 formed in the lower support member, thus comprising a lower portion of the second support means 490. Similarly, as in the case of the third embodiment of the apparatus, the cap 522 includes inlet condui means 524 outlet conduit means 526, a sampling port 528 sealed with a self-resealing cap 530, and a loop 532 for engaging the pin 496 projecting from upper support member 494, comprising an upper portion of the second support means. The generally helical support members 504 are positioned within the wall 502 of the helical collector 500 in the illustrated embodiment. However, the wall could also be supported by one or more helical support members positioned exteriorally of the wall, the wall including, for example, one or more corresponding helical pockets formed therein for insertion of the helical support members, or a plurality of tabs positioned on the exterior of the wall for engaging the helical support members to support the wall.

Figure 15:
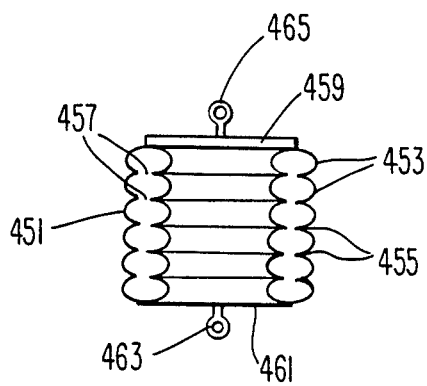
FIG. 15 is a schematic illustration of another embodiment of a collection apparatus of this invention.

In addition, other means can be used to confer transverse rigidity on the wall. For example the wall can simply be formed from a flexible material and securely attached to a pair of substantially rigid ends, one end being releasably attached to a portion of a second support means by a biasing means, such as a spring, for exerting tension on the wall to at least partially balance the pressure differential force tending to cause the wall to collapse when a vacuum is drawn in the interior cavity (not shown). Alternatively, as in FIG. 15, the wall 451 itself can have a tubular structure formed from at least two generally coaxial tubes 453 of flexible material attached together at a plurality of points 455 but forming a generally continuous chamber therebetween, with openings 457 connecting the tubes, the wall being inflatable to provide rigidity to the tubular structure to at least partially counterbalance the pressure differential force tending to cause the wall to collapse, and with a preferably rigid disk 459 sealing closed the upper end, and with a preferably flexible web 461 (or rigid disk) sealing closed the lower end, which end has suitable spike ports (not shown) therein, with hangers 463 and 465 also being shown.

Figure 16:
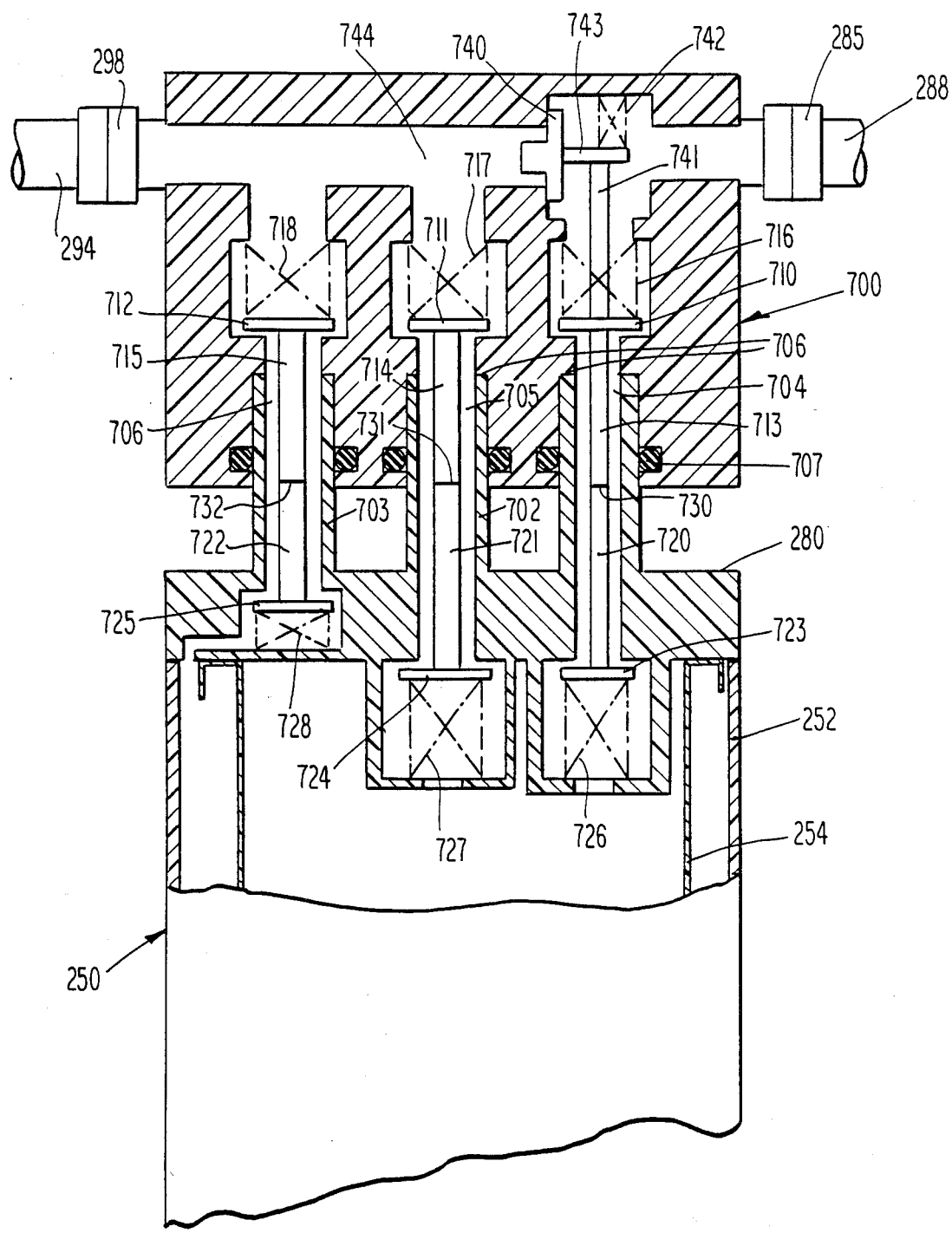
FIG. 16 is a fragmentary schematic illustration of an interconnect unit with apparatus of this invention for optimal use with collectors in accordance with the embodiments of this invention.

With particular reference now to FIG. 16, there is illustrated in fragmentary cross-section, an interconnect manifold 700, as an alternative way of connecting the tubes 288, 294 to the autotransfusion collector 250, to allow for quick connection and disconnection, with simultaneous sealing closed the vacuum and liquid inlet connections to the collector 250, along with the simultaneous sealing closed of the vacuum openings and blood inlet opening from the manifold 700, and further along with the simultaneous opening of fluid communication between the lines 288 and 294, when the disconnection with the collector 250 is effected, to allow for liquid flow from the line 288 to the line 294, and hence into chamber 115, for example, when the disconnection is effected. To this end, the cap 280 is provided with upstanding annular cylindrical members 701, 702 and 703, that extend into corresponding bores 704, 705 and 706, in the interconnect member 700 sealingly received within O-rings 707 in those bores, and with the members 701, 702 and 703, being suitably seated at upper ends, such as 706 of those bores. Upon such seating, slidable valves 710, 711 and 712, with attached depending valve stems 713, 714 and 715, are biased downwardly by springs 716, 717 and 718, such that the stems engage upstanding stems 720, 721 and 722 of valves 723, 724 and 725, likewise spring-biased upwardly by means of compression springs 726, 727 and 729, along parting lines 730, 731 and 732, such that when the cylindrical members are seated within the bores, as illustrated, all of the valves are pressed open somewhat, as shown, against the forces provided by their associated springs. Thus opened, vacuum drawn via line 294 will draw vacuum through cylindrical member 702, from the inside of the inner receptacle 254, thereby drawing blood or other liquid from line 288, through the manifold, through cylindrical member 701, past valve 723, into inner receptacle 254, in that valve 740 is seated as shown. In instances when the apparatus of FIG. 16 is used with a system involving the continuous application of vacuum, as in the phantom portion of the illustration of FIG. 13 described above, valves 712 and 725 will be used, along with their companion bores, etc., as illustrated in FIG. 16. In instances in which the receptacle 254 is hermetically sealed as in the solid line illustration of FIG. 13, the valves 712, 725, and their companion bores, etc., are not necessary for the interconnect manifold 700. When the cap 280 is disconnected from the manifold 700, and valves 712, 711 and 710 become seated, valve 710 pulls stem 741 downwardly therewith, assisted by spring 742, thereby pulling stem 743 downwardly and unseating valve 740, allowing communication from line 288 directly to line 294, via passage way 744. Thus, the collector 250 can be removed from the manifold, and remain in a sealed condition relative to atmosphere, and the manifold itself can remain sealed relative to atmosphere, with the body liquid being otherwise collected, passing through the manifold 700.

The process of the present invention employs the apparatus of the various embodiments described above in collecting and storing blood for optional blood reuse as for autotransfusion. In general, the present invention provides a process for the collection of blood from a body cavity, the process includes the step of placing the inlet of a controllable flow conduit having an inlet and an outlet in a body cavity from which blood is to be withdrawn. For example, the controllable flow conduit can include a section of flexible tubing 288, and the first portion 286a of the first detachable connection means 286, and the first control means 290 illustrated in FIGS. 1, 2, 4, 6, 7 and 9. The inlet to the flow conduit can be a suction wand of the type generally used in collecting blood from body cavities (not shown). The controllable flow conduit can include means for mixing anticoagulant solutions, such as citrate-phosphate-dextrose solution, with the blood drawn from the body cavity to retard or prevent coagulation thereof (not illustrated). Appropriate metering means can be provided in the flow conduit for mixing the anticoagulant solution with the blood drawn from the body cavity (not shown).

Another step in the process of the present invention includes connecting the outlet of the controllable flow conduit to the inlet of a blood collection apparatus to place the body cavity in fluid communication with the blood collection apparatus. For example, when the outlet of the controllable flow conduit comprises the first portion 286a of the first connector means 286 the process includes the step of connecting the first portion 286a to the second portion 286b of the first connector means 286. In this case the blood collection apparatus includes the second portion 286b of the second connector means 286 as well as the second flexible tubing section or inlet tube 282 connecting the first connection means 286 to the inlet conduit means 274 of the autotransfusion collector (FIGS. 1-2, 4), the accordion collector 450 (FIGS. 6-7), or helical collector 500 (FIG. 9).

The process of the present invention also includes applying suction to the first opening in the apparatus body 100. Because the interior cavity of the transfusion collector 250, accordion collector 450, or helical collector 500, is in fluid communication through the sealing means with the first opening in the apparatus body 100, suction is thus applied to the interior cavity of the autotransfusion collector 250, accordion collector 450, or helical collector 500, respectively.

The process further includes opening the first control means in the controllable flow conduit, such as the first control means or clamping means 290 provided in the first flexible tubing section 288, to permit blood to flow from the body cavity through the controllable flow conduit nd into the inner cavity of the inner receptacle of the autotransfusion collector 250, the accordion collector 450, or the helical collector 500.

When the apparatus of the first embodiment is employed in the present process, the flexible wall 258 of the inner receptacle 254 will collapse slightly when suction is applied to the interior cavity 256, unless the intermediate cavity 270 has been previously evacuated to a pressure below that of the applied suction. However, as long as a good air-tight seal is maintained between the outer and inner receptacles 252, 254, the intermediate cavity 270 need not be evacuated prior to practicing the process of the present invention.

When suction is applied to the interior cavity 256 the wall 258 will collapse until the pressure within the interior cavity 256 of the inner receptacle 254 is approximately equal to the pressure within the intermediate cavity 270 between the wall 258 and the outer receptacle 252. Because the volume of the intermediate cavity 270 is preferably minimized as described above, it is relatively small in comparison with the volume of the interior cavity 256. A decrease in the volume of the interior cavity 256 will be accompanied by an increase in the volume of the intermediate cavity 270. However, a relatively small decrease in volume of the interior cavity 256 in comparison with the magnitude of the total volume of the interior cavity 256 will correspond to a relatively large increase in the volume of the intermediate cavity 270. The product of the pressure and the volume of the intermediate cavity 270 must be a constant at constant temperature according to the gas laws. Consequently, only a small increase in volume of the intermediate cavity 270 is required before the pressure of the gas contained within the intermediate cavity 270 drops to equal the pressure of the gas within the interior cavity 256 under the applied suction. Because the material from which the flexible wall 258 separating the interior cavity 256 and intermediate cavity is formed is relatively impermeable to gas over relatively short periods of time, such as the time required to fill the interior cavity 256 with blood 260, the volume of the interior cavity 256 is only slightly diminished by the application of suction thereto and the scale 251 formed in the outer receptacle 252 gives a generally accurate measure of the volume of blood 260 contained within the inner receptacle 254 while blood 260 is being collected.

In the third and fourth embodiments of the apparatus of the present invention described above, the collection vessels or receptacles are also adapted to exhibit minimum volume change when suction is applied to the interior cavities 456, 518 thereof. However, it should be noted that in most of the embodiments of the apparatus of the present invention is it required to apply a countervailing suction to maintain the collection receptacles in an uncollapsed condition during blood collection.

After the inner receptacle 254 has been filled with blood 260 to a predetermined level, or when it is otherwise desired to change the autotransfusion collector 250, the first, second and third control means, 290, 284 and 296 are closed, and the first and second connector means 286, 298 are separated into their constituent sections 286a, 286b and 298a, 298b, respectively. The portions 296b, 298a of the first and second connection means 286, 298 remaining with the autotransfusion collector 250 can be connected together, if desired. The inner receptacle 254 is released from the outer receptacle 252 by removing the receptacle sealing means 268 to permit the partial vacuum within the intermediate cavity 270 to be released. The receptacle sealing means 268 thus also constitutes a vacuum release means. If additional sealing means is provided between the inner and outer receptacles 254, 252 it may be necessary to exert a small amount of force in pulling the inner receptacle 254 out of the outer receptacle 252 against the partial vacuum in the interior cavity 270. If desired, an additional port can be provided in the outer receptacle to release the vacuum (not shown).

Figure 10:
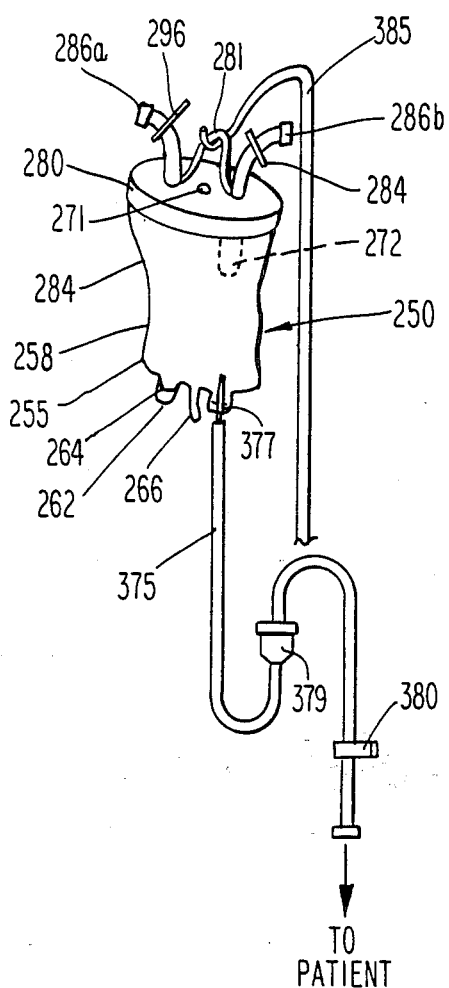
FIG. 10 is a fragmentary perspective view of the autotransfusion collector of FIGS. 1–3 shown delivering blood to a patient.

As illustrated in FIG. 10, a standard infusion set 375 is connected to the inner receptacle 254 to place the interior cavity 256 of the inner receptacle 254 in fluid communication with the interior of the infusion set 375 by inserting the needle 377 of the infusion set 375 into one of the sealed ports or spike ports 264 formed in the sealed end 255 of the wall 258 of inner receptacle 254. The inner receptacle 254 fitted with the infusion set 375 is then suspended in a positioned elevated relative to the patient such as by placing the loop 281 over the arm of a standard IV stand 385. The infusion set 375 is primed using a saline solution (not shown) or the blood 260 contained within the inner receptacle 254 as desired. After the inner receptacle 254 has been detached from the outer receptacle 252, residual air is displaced from the interior cavity 256 of the inner receptacle 254 through the infusion set 375 or alternatively, but less preferably, by opening the third control means 296 and squeezing the wall 258 until all the air within the interior cavity 256 is displaced through the outlet conduit means 276 and associated outlet tube 294. The interior of the infusion set 375 is placed in adjustable fluid communication with a body cavity of the patient. Preferably, a filter 379 is employed in the infusion set 375 to filter out foreign materials, microembolisms, and the like for the safety of the patient. The rate of blood flow from the inner receptacle 254 to the body cavity is adjusted to a predetermined rate using valve means 380. If desired, the wall 258 of the inner receptacle 254 can be fitted with a standard pressure cuff (not illustrated) to speed the rate of delivery of blood from the inner receptacle 254.

Various modifications can be made in the details of the construction, the use and operation of the various embodiments of the apparatus of the present invention, and the process employing these embodiments, all within the spirit and scope of the invention as defined in the appended claims.

What is claimed is:

1. A method of collection of blood for reuse thereof comprising:
   (a) providing a receptacle having a fluid filter therein for receiving blood in an interior thereof;
   (b) providing support means for said receptacle;
   (c) arranging said receptacle within said support means so as to provide a zone defined between said receptacle and said support means;
   (d) maintaining said zone
      (i) hermetically sealed from the atmosphere and from the source of vacuum and
      (ii) hermetically sealed from the interior of said receptacle;
   (e) delivering blood to said receptacle through an inlet thereof; and
   (f) applying a source of vacuum to said receptacle to draw blood through said filter and into said receptacle.

2. The method of claim 1, including the step of venting the zone to atmosphere for removal of the receptacle from the support means.

3. The method of claim 1, including sensing, displaying and controlling the vacuum during use.

4. Apparatus for the collection of blood for reuse thereof comprising:
   (a) a receptacle for receiving blood in an interior thereof;
   (b) support means for said receptacle;
   (c) a zone defined between said receptacle and said support means;
   (d) means maintaining said zone
      (i) hermetically sealed from the atmosphere and from the source of vacuum and
      (ii) hermetically sealed from the interior of said receptacle;
   (e) an inlet to said receptacle for the delivery of blood therethrough;
   (f) means for applying a source of vacuum to the apparatus to draw blood through a said filter and into said receptacle; and
   (g) a filter as part of the apparatus for filtering blood drawn therethrough.

5. The apparatus of claim 4, wherein a plurality of collection receptacles with inlets are provided, with means for selectively switching the delivery of blood among said inlets.

6. The apparatus of claim 4, wherein said filter is located within said receptacle.

7. The apparatus of claim 4, wherein said receptacle is disposed within said support means.

8. The apparatus of claim 4, wherein said receptacle and said support means are separable from each other.

9. The apparatus of claim 4, including means for venting said zone to the atmosphere for facilitating removal of said receptacle from said support means.

10. The apparatus of claim 4, including means for compressing said receptacle for facilitating discharge of blood therefrom.

11. The apparatus of claim 10, wherein said means for compressing comprise bladder means and means for inflating said bladder means.

12. The apparatus of claim 4, with the apparatus further including a vacuum monitoring means for sensing, controlling and displaying the vacuum drawn during use.

13. The apparatus of claim 4, wherein said support means is substantially rigid.

14. The apparatus of claim 13, wherein said receptacle includes a substantially rigid cap and a substantially flexible, generally tubular bag, one end of which is hermetically sealed to said cap.

15. The apparatus of claim 4, wherein vacuum control means is provided with said means for applying a source of vacuum, and with a sealing means being operatively located between said vacuum control means and said receptacle.

16. The apparatus of claim 15, wherein said vacuum control means is a manometer.

17. The apparatus of claim 15, wherein said sealing means comprises a water seal.

18. The apparatus of claim 15, wherein at least one collection chamber is provided between said receptacle and said sealing means.

19. The apparatus of claim 18, wherein said vacuum control means, said sealing means and said at least one collection chamber comprise a unit, detachably connectible to said support means.

20. The apparatus of claim 15, wherein said vacuum control means and said sealing means comprise a unit detachably connectible to said support means.

21. The apparatus of claim 19, wherein said vacuum control means, said sealing means, said at least one collection chamber, and said receptacle support means comprise an integral unit.

22. The apparatus of claim 15, wherein said vacuum control means, said sealing means and said receptacle support means comprise an integral unit.

23. A method of collecting blood and certain other body fluids, comprising the steps of:
   (a) providing a vacuum opening component connected to a source of suction;
   (b) providing a support component having a flexible collection receptacle therein for receiving blood;
   (c) providing sealing means that permits gas to be transmitted therethrough, with one side of said sealing means in communication with said vacuum opening and with the other side in communication with said flexible collection receptacle within said support component;
   (d) delivering blood or certain other body fluids to an inlet of said receptacle;
   (e) filtering the blood or other fluids as it enters the receptacles;
   (f) applying a vacuum from said source to draw blood or other fluids into said receptacle; and (g) maintaining said support component outside said flexible collection receptacle hermetically sealed from communication with atmosphere and said source of suction.

24. The method of claim 23, including the step of monitoring and controlling the vacuum drawn through the vacuum opening, by means of a manometer.

25. Apparatus for collection of blood for reuse thereof, comprising:
   (a) a vacuum opening component for connection to a source of suction;
   (b) a flexible collection receptacle having a fluid filter in fluid communication therewith;
   (c) gas-transmitting sealing means with one side in communication with said vacuum opening and the other side in communication with said flexible collection receptacle for receiving and collecting blood through said filter, and with means maintaining said support component outside said flexible collection receptacle hermetically sealed from communication with atmosphere and said source of suction.

26. The apparatus of claim 25, including a manometer constructed as a component of the same single integral unit, for monitoring and controlling the vacuum drawn through the vacuum opening.

27. The apparatus of claim 25, including at least one chamber in addition to said collection receptacle support component, to collect blood, said chamber being in communication with said other side of said sealing means.

28. The apparatus of claim 25, wherein said receptacle is disposed within said support means.

29. The apparatus of claim 25, wherein said receptacle and said support means are separable from each other.

30. The apparatus of claim 25, including means for venting said zone to atmosphere.

31. The apparatus of claim 25, including means for compressing said receptacle for facilitating discharge of blood therefrom.

32. The apparatus of claim 25, wherein said means for compressing comprise a bladder means and means for inflating said bladder means.

33. The apparatus of claim 25, wherein the receptacle includes a substantially rigid cap and a substantially flexible, generally tubular bag, one end of which is hermetically sealed to said cap.

34. The apparatus of claim 25, including means for adding a reagent to said receptacle through said filter.

35. The apparatus of claim 25, including other sealing means in fluid connection with said apparatus, for preventing flow of liquid from other locations in said apparatus into said collection receptacle.

36. The apparatus of claim 25, wherein a plurality of collection receptacles with inlets are provided, and having means for selectively switching the delivery of blood among said inlets.

37. Apparatus for the collection of certain body fluids comprising:
   (a) a receptacle for receiving body fluids in an interior thereof;
   (b) a support means for the receptacle;
   (c) a filter for fluid entering the receptacle and means for adding a reagent to the receptacle through the filter;
   (d) a zone defined between the receptacle and support means;
   (e) means maintaining said zone
      (i) hermetically sealed against atmosphere; and from the source of vacuum and
      (ii) hermetically sealed from the interior of the receptacle;
   (f) an inlet to the receptacle for the delivery of body fluids therethrough; and
   (g) means for applying a source of vacuum to the apparatus to draw body fluids into the receptacle.

38. Apparatus for the collection of certain body fluids comprising:
   (a) a receptacle for receiving body fluids in an interior thereof;
   (b) a support means for the receptacle;
   (c) a zone defined between the receptacle and support means;
   (d) means maintaining said zone
      (i) hermetically sealed against atmosphere; and from the source of vacuum and
      (ii) hermetically sealed from the interior of the receptacle;
   (e) an inlet to the receptacle for the delivery of body fluids therethrough;
   (f) means for applying a source of vacuum to the apparatus to draw body fluids into the receptacle; and
   (g) a bladder means and means for inflating said bladder means for compressing said receptacle and facilitating discharge of body fluids therefrom.

39. Apparatus for the collection of certain body fluids comprising:
   (a) a receptacle for receiving body fluids in an interior thereof;
   (b) a support means for the receptacle;
   (c) a zone defined between the receptacle and support means;
   (d) means maintaining said zone
      (i) hermetically sealed against atmosphere; and and from the source of vacuum
      (ii) hermetically sealed from the interior of the receptacle;
   (e) an inlet to the receptacle for the delivery of body fluids therethrough; and
   (f) means for applying a source of vacuum to the apparatus to draw body fluids into the receptacle wherein said support means are comprised of collapsible membrane means, with means facilitating the inflation of said support means for the performance of its supporting function.

40. Apparatus for the collection of certain body fluids comprising:
   (a) a receptacle for receiving body fluids in an interior thereof;
   (b) a support means that is substantially rigid for the receptacle;
   (c) a zone defined between the receptacle and support means;
   (d) means maintaining said zone
      (i) hermetically sealed against atmosphere; and from the source of vacuum
      (ii) hermetically sealed from the interior of the receptacle;
   (e) an inlet to the receptacle for the delivery of body fluids therethrough; and
   (f) means for applying a source of vacuum to the apparatus to draw body fluids into the receptacle wherein the receptacle includes a substantially rigid cap and a substantially flexible, generally tubular bag, one end of which is hermetically sealed to the cap.

41. Apparatus for collection of certain body fluids comprising:
  (a) a vacuum opening component for connection to a source of suction;
  (b) a collection receptacle support component;
  (c) a gas-transmitting sealing means component, with one side in communication with said vacuum opening and the other side in communication with a flexible collection receptacle for receiving and collecting body fluids through an inlet thereof, with said support component, and with said components being constructed as components of a single integral unit wherein a zone is defined between said flexible collection receptacle support component and the receptacle disposed therein; with means maintaining said zone;
    (i) hermetically sealed against atmosphere; and from the source of vacuum
    (ii) hermetically sealed from the receptacle.

42. Apparatus for collection of certain body fluids comprising:
  (a) a vacuum opening component for connection to a source of suction;
  (b) a collection receptacle support component;
  (c) a gas-transmitting sealing means component, with one side in communication with said vacuum opening and the other side in communication with a flexible collection receptacle for receiving and collecting body fluids through an inlet thereof, with said support component, and with said components being constructed as components of a single integral unit wherein a zone is defined between said flexible collection receptacle support component and the receptacle disposed therein; with means maintaining said zone;
    (i) hermetically sealed against atmosphere; and from the source of vacuum
    (ii) hermetically sealed from the receptacle; and wherein said receptacle is disposed within said support means.

43. Apparatus for collection of certain body fluids comprising:
  (a) a vacuum opening component for connection to a source of suction;
  (b) a collection receptacle support component;
  (c) a gas-transmitting sealing means component, with one side in communication with said vacuum opening and the other side in communication with a flexible collection receptacle for receiving and collecting body fluids through an inlet thereof, with said support component, and with said components being constructed as components of a single integral unit wherein a zone is defined between said flexible collection receptacle support component and the receptacle disposed therein; with means maintaining said zone;
    (i) hermetically sealed against atmosphere; and from the source of vacuum
    (ii) hermetically sealed from the receptacle. and wherein said receptacle and said support means are separable from each other.

44. Apparatus for collection of certain body fluids comprising:
  (a) a vacuum opening component for connection to a source of suction;
  (b) a collection receptacle support component;
  (c) a gas-transmitting sealing means component, with one side in communication with said vacuum opening and the other side in communication with a flexible collection receptacle for receiving and collecting body fluids through an inlet thereof, with said support component, and with said components being constructed as components of a single integral unit wherein a zone is defined between said flexible collection receptacle support component and the receptacle disposed therein; with means maintaining said zone;
    (i) hermetically sealed against atmosphere; and from the source of the vacuum
    (ii) hermetically sealed from the receptacle; and including means for compressing said receptacle for facilitating discharge of body fluids therefrom.

45. Apparatus for collection of certain body fluids comprising:
  (a) a vacuum opening component for connection to a source of suction;
  (b) a collection receptacle support component;
  (c) a gas-transmitting sealing means component, with one side in communication with said vacuum opening and the other side in communication with a flexible collection receptacle for receiving and collecting body fluids through an inlet thereof, with said support component, and with said components being constructed as components of a single integral unit wherein a zone is defined between said flexible collection receptacle support component and the receptacle disposed therein; with means maintaining said zone;
    (i) hermetically sealed against atmosphere; and from the source of the vacuum
    (ii) hermetically sealed from the receptacle;
  and including bladder means and means for inflating said bladder means for compressing said receptacle for facilitating discharge of body fluids therefrom.

46. Apparatus for collection of certain body fluids comprising:
  (a) a vacuum opening component for connection to a source of suction;
  (b) a collection receptacle support component;
  (c) a gas 0transmitting sealing means component, with one side in communication with said vacuum opening and the other side in communication with a flexible collection receptacle for receiving and collecting body fluids through an inlet thereof, with said support component, and with said components being constructed as components of a single integral unit wherein a zone is defined between said flexible collection receptacle support component and the receptacle disposed therein; with means maintaining said zone;
    (i) hermetically sealed against atmosphere; and from the source of the vacuum
    (ii) hermetically sealed from the receptacle; and wherein the receptacle includes a substantially rigid cap and a substantially flexible, generally tubular bag, one end of which is hermetically sealed to the cap.

* * * * *